United States Patent [19]

Yamada et al.

[11] Patent Number: 4,578,171

[45] Date of Patent: Mar. 25, 1986

[54] AIR/FUEL RATIO DETECTOR

[75] Inventors: Tetsusyo Yamada; Shintaro Hirate, both of Aichi, Japan

[73] Assignees: NGK Spark Plug Co., Ltd.; Mitsubishi Denki Kabushiki Kaisha, both of Japan

[21] Appl. No.: 681,338

[22] Filed: Dec. 13, 1984

[30] Foreign Application Priority Data

Dec. 15, 1983 [JP] Japan .............................. 58-237624
Dec. 15, 1983 [JP] Japan .............................. 58-237625

[51] Int. Cl.$^4$ ........................................... G01N 27/58
[52] U.S. Cl. .................................. 204/406; 204/410; 204/412
[58] Field of Search ............... 204/412, 410, 424, 425, 204/426, 427, 428, 429, 15, 406; 60/276; 123/489

[56] References Cited

U.S. PATENT DOCUMENTS

| | | | |
|---|---|---|---|
| 4,158,166 | 6/1979 | Isenberg | 204/426 X |
| 4,264,425 | 4/1981 | Kimura et al. | 204/412 |
| 4,298,573 | 11/1981 | Fujishiro | 204/412 X |
| 4,450,065 | 5/1984 | Yamada et al. | 204/412 |

Primary Examiner—G. L. Kaplan
Attorney, Agent, or Firm—Sughrue, Mion, Zinn, Macpeak, and Seas

[57] ABSTRACT

An A/F ratio detector capable of accurately and unambiguously detecting the operating A/F ratio of a burner such as an internal combustion engine whether the engine is operating in the fuel-rich region, fuel-lean region or at the theoretical A/F ratio. The detector includes a solid-electrolyte oxygen pump element having a porous electrode formed on both sides of an oxygen-ion-conductive solid electrolyte, and a solid-electrolyte oxygen-concentration-difference-actuated electrochemical cell sensor element disposed to face the pump element with a small gap therebetween and which has two porous electrodes formed on opposite sides of an oxygen-ion-conductive solid electrolyte. An air compartment open to the atmosphere is formed on a side of the electrochemical cell sensor element opposite the small gap. The electromotive force generated by one pair of the porous electrodes on the electrochemical cell sensor element, the pump current flowing through the other pair of porous electrodes on the sensor element, or the pump current flowing through the porous electrodes on the pump element provides an output signal for A/F ratio detection.

8 Claims, 12 Drawing Figures

AIR/FUEL RATIO DETECTOR

BACKGROUND OF THE INVENTION

The present invention relates to an A/F (Air/Fuel) ratio detector for use in the measurement or control of the concentration of oxygen in exhaust gas from a burning device such as an internal combustion engine or gas burner.

An oxygen sensor composed of an oxygen-ion-conductive solid electrolyte (e.g., stabilized zirconia) coated with porous electrode layers (e.g., Pt porous layers) is capable of detecting the concentration of oxygen near a theoretical (stoichiometric) A/F ratio of exhaust gas from an internal combustion engine to thereby detect the combustion efficiency of the engine. Detection is carried out by sensing a change in an electromotive force that is produced by the difference between the partial oxygen pressure of the exhaust gas and that of atmospheric air. This type of oxygen sensor is presently used in numerous applications, for example, in an automobile for the purpose of controlling its internal combustion engine to run at the theoretical air/fuel ratio.

The conventional oxygen sensor exhibits a large amount of change in its output if the operating A/F ratio (which is the weight ratio of air to fuel) is near the theoretical value of 14.7, but otherwise the resulting change in output is negligibly small. Therefore, the output from this sensor cannot be effectively used for an engine operating at an A/F ratio other than near the theoretical value.

Japanese Published Unexamined Patent Application No. 153155/1983 shows an oxygen concentration detector composed of a pair of oxygen-ion-conductive solid electrolyte plates each having an electrode layer on both sides in a selected area close to one end thereof. The two plates are fixed parallel to each other and spaced to provide a gap in an area corresponding to that selected area having the electrode layers. One electrolyte plate with electrode layers is used as an oxygen pump element, and the other plate also having electrode layers is used as an electrochemical cell sensor element that operates in response to the difference in oxygen concentration between the ambient atmosphere and the gap between the two plates. This type of detector has a quick response, but according to experiments conducted by the present inventors, the output of the sensor is ambiguous. That is, when this device is operated in a fuel-rich region having an A/F ratio lower than the theoretical value of 14.7, the direction of change of the output away from the theoretical value is the same as that for operation in the fuel-lean region. Because of the existence of two possible A/F ratios for a single output, the sensor can be used only when it is definitely known whether the burning device to be controlled is operating in the fuel-rich or fuel-lean region.

SUMMARY OF THE INVENTION

Accordingly, an object of the present invention is to provide an A/F ratio detector that is capable of accurately detecting the operating A/F ratio of a burner such as an internal combustion engine whether it is operating in the fuel-rich region, fuel-lean region or at the theoretical A/F ratio.

Another object of the present invention is to provide an A/F ratio detector that enables precise and simple feedback control over the A/F ratio.

The above and other objects of the present invention are met by an A/F ratio detector comprising a solid electrolyte oxygen pump element having a porous electrode formed on both sides of an oxygen-ion-conductive solid electrolyte and a solid-electrolyte oxygen-concentration-difference-actuated electrochemical cell sensor element which is disposed to face the pump element with a small gap therebetween and which has two pairs of porous electrodes formed on an oxygen-ion-conductive solid electrolyte, the small gap communicating with ambient gases, means defining air compartments open to the atmosphere on that side of at least the electrochemical cell sensor element of the two elements which side is opposite the small gap, a current of such direction that oxygen is supplied into the small gap being applied between either the electrodes of one of the two pairs or the electrodes of the pump element, a current of such direction that oxygen is pumped out from the small gap being applied between the electrodes of the one of the two pairs or of the pump element other than the electrodes to which is applied the current of such direction that oxygen is supplied into the small gap, one of an electromotive force generated by the other pair of electrodes of the electrochemical cell sensor element, the current of such direction that oxygen is pumped out from the small gap, and the current of such direction that oxygen is supplied into the small gap providing an output signal for A/F ratio detection.

According to another aspect of the present invention, there is provided an A/F ratio detector comprising a solid-electrolyte oxygen pump element having two pairs of porous electrodes formed on an oxygen-ion-conductive solid electrolyte and a solid-electrolyte oxygen-concentration-difference-actuated electrochemical cell sensor element which is disposed to face the pump element with a small gap therebetween and which has porous electrodes formed on both sides of an oxygen-ion-conductive solid electrolyte, the small gap communicating with ambient gases, means defining air compartments open to the atmosphere on that side of at least the electrochemical cell sensor element of the two elements which side is opposite the small gap, a current of such direction that oxygen is supplied into the small gap being applied between the electrodes of one of the two pairs, a current of such direction that oxygen is pumped out from the small gap being applied between the electrodes of the other pair, one of an electromotive force generated by the electrodes of the electrochemical cell sensor element, the current of such direction that oxygen is pumped out from the small gap, and the current of such direction that oxygen is supplied into the small gap providing an output signal for A/F ratio detection.

With the arrangement above, the detector of the present invention has the advantage of enabling the A/F ratio to be controlled at a desired level, whether it is in the fuel-rich region, fuel-lean region or at the theoretical value of 14.7, by providing an accurate detection signal that corresponds to the actual A/F ratio. The detector achieves this result without changing, from positive to negative or vice versa, the direction of voltage or current that is being applied to the porous electrodes of the pump element or the electrochemical cell sensor element.

DESCRIPTION OF THE PREFERRED EMBODIMENTS

Preferred embodiments of an A/F ratio detector of the present invention will hereunder be described with reference to the accompanying drawings.

Figure 1:
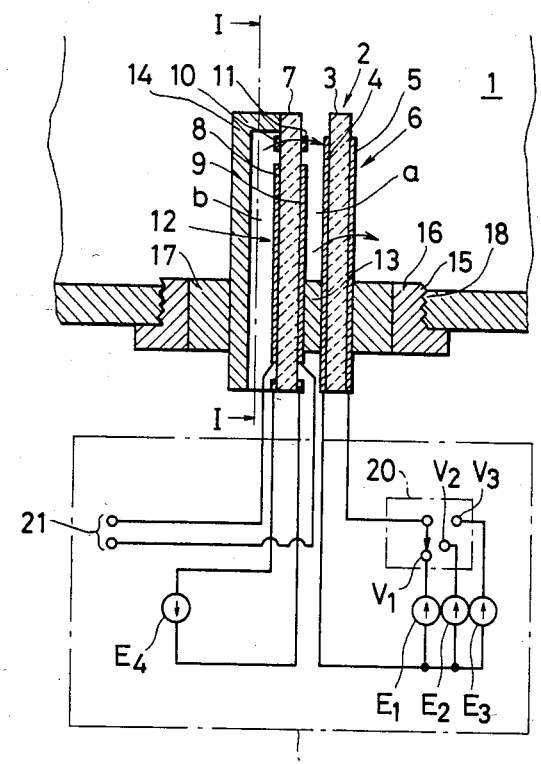
FIG. 1 shows, in cross section, an A/F ratio detector according to a first preferred embodiment of the present invention.
Figure 2:
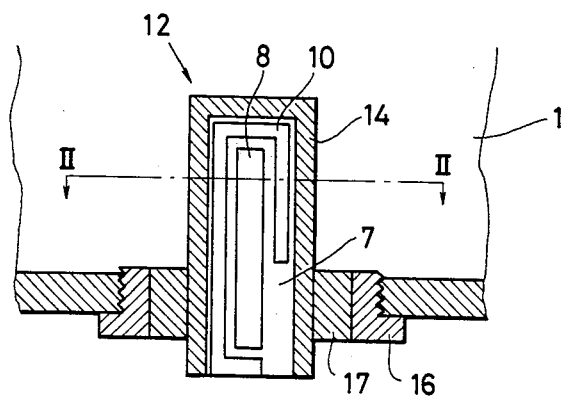
FIG. 2 is a cross section taken along a line I—I in FIG. 1.
Figure 3:
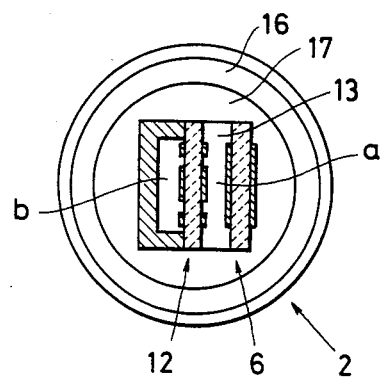
FIG. 3 is a cross section taken along a line II—II of FIG. 2.

FIGS. 1, 2 and 3 show a detector according to a first preferred embodiment of the invention. The detector is mounted in an exhaust pipe 1 of an internal combustion engine. The probe 2 of the detector includes a solid-electrolyte oxygen pump element 6 and a solid-electrolyte oxygen-concentration-difference-actuated electrochemical cell sensor element 12. The pump element 6 consists of an ion-conductive solid-electrolyte plate 3 (about 0.5 mm thick and preferably made of stabilized zirconia) having a porous Pt electrode layer 4 formed on one side and another porous Pt electrode layer 5 formed on the other side. Each Pt layer has a thickness of about 20 μm and may be formed by a thick-film deposition technique. The electrochemical cell sensor element 12 also consists of an ion-conductive solid-electrolyte plate 7 (about 0.5 mm thick and preferably made of stabilized zirconia) having two porous platinum electrode layers 8 and 10 formed on one side and two porous Pt electrode layers 9 and 11 formed on the other side.

The layers 8 and 9 together constitute a first pair of electrodes, and the layers 10 and 11 together constitute a second pair. The first pair of electrodes 8 and 9 is located at the center of the solid electrolyte plate 7, whereas the second pair of electrodes 10 and 11 is disposed around and spaced from the electrodes 8 and 9.

The pump element 6 and the sensor element 12 are mounted side by side in the exhaust pipe 1 with a gap a therebetween, typically about 0.1 mm or less in width, and are fixed together by filling the gap at the base portion with a heat-resistive and insulating spacer 13. An adhesive filler may be used as the spacer. The peripheral portion of the solid electrolyte plate 7 on the side opposite the gap from the pump element 6 is attached to a wall 14 made of a heat-resistive and gas-impermeable material such as a metal or ceramic to form an air compartment b which allows the porous Pt electrode layers 8 and 10 to communicate with the atmosphere.

A support 16 with a male thread 15 is fixed around the base portion of the combined pump element 6, sensor element 12 and wall 14 by means of a heat-resistive and insulating adhesive member 17. The probe 2 is securely mounted in the exhaust pipe 1 by engaging the male thread 15 with a female thread 18 in the exhaust pipe 1.

An example of an electronic control unit for use in association with the detector according to the first embodiment of the present invention is indicated in FIG. 1 by reference numeral 19. The porous Pt electrode layers 4 and 5 on the pump element 6 are connected to a switch 20 which selectively actuates constant current sources $E_1$, $E_2$ and $E_3$ ($E_1 < E_2 < E_3$) that provide currents for pumping oxygen out of the small gap a into the exhaust pipe 1. The switch 20 has three positions $V_1$, $V_2$ and $V_3$ which respectively provide connection to the constant current sources $E_1$, $E_2$ and $E_3$. The pair of porous Pt electrode layers 8 and 9 of the cell sensor element 12 are connected at one end to output terminals 21 for sensing the electromotive force e generated across these electrode layers. The other pair of porous Pt electrode layers 10 and 11 are connected at one end to a constant current source $E_4$ for pumping oxygen into the small gap a from the air compartment b. In the embodiment shown, the ability of the current source $E_2$ to pump oxygen out of the small gap a into the exhaust pipe 1 is made substantially equal to the ability of the current source $E_4$ to pump oxygen into the small gap a from the air compartment b.

Figure 4:
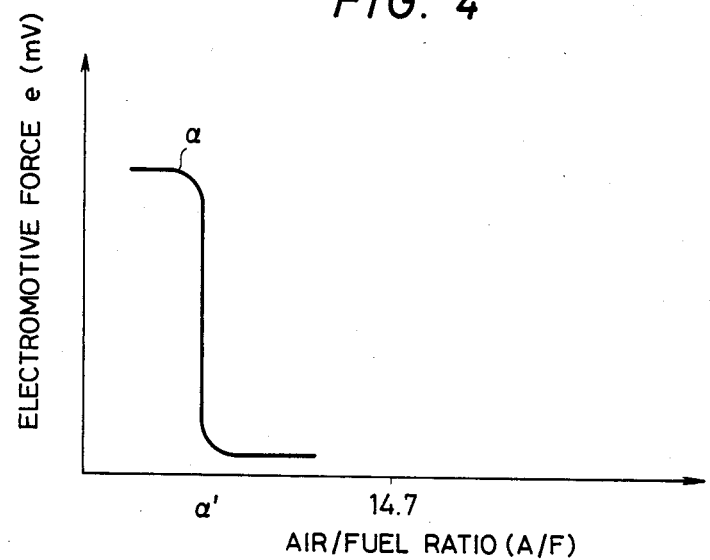
FIGS. 4 to 6 are characteristic curves for the first embodiment of the present invention showing the A/F ratio vs. the EMF e of one pair of porous Pt electrode layers on the oxygen-concentration-difference-actuated electrochemical cell sensor element, with the pump-in current that flows through the other pair of porous Pt electrode layers on the electrochemical cell sensor element being held constant and the pump-out current flowing through the oxygen pump element being changed to three different levels.
Figure 5:
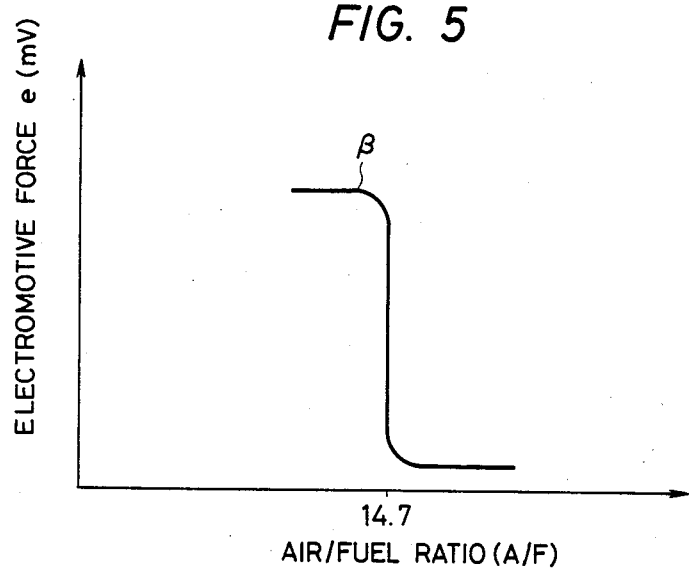
Figure 6:
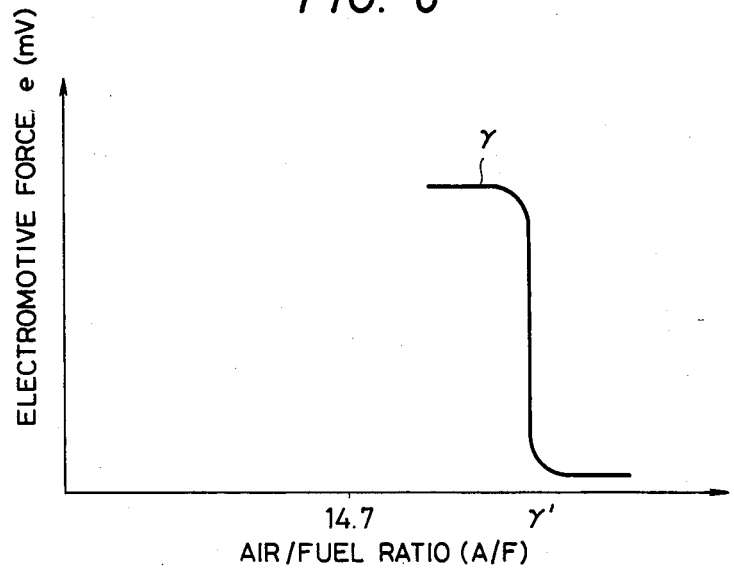

Three characteristic curves for the A/F ratio detector shown in FIGS. 1 to 3 are illustrated in FIGS. 4 to 6. It is first assumed that the switch 20 is set to the position $V_1$ connecting the constant current source $E_1$ to the porous Pt electrode layers 4 and 5 on the pump element 6 in the detector probe 2 mounted in the exhaust pipe 1. Since the ability of the electrode layers 4 and 5 to pump oxygen out of the small gap a into the exhaust pipe 1 is less than the ability of the pair of porous Pt electrode layers 10 and 11 on the electrochemical cell sensor element 12 to pump oxygen into the small gap a from the air compartment b, the electromotive force e generated across the other pair of electrode layers 8 and 9 on the cell sensor element 12 and which is sensed at the output terminals 21 drops suddenly at an A/F ratio $\alpha'$ in the fuel rich region as illustrated in FIG. 4. When the switch 20 is set to the position $V_2$ connecting the Pt electrode layers 4 and 5 to the current source $E_2$, the electromotive force e sensed at the output terminals 21 also drops suddenly, but this time at an A/F ratio $\beta'$ near the theoretical value of 14.7 (see FIG. 5), which is a critical point for the concentration of oxygen in the exhaust gas in the pipe 1. This is due to the ability of the electrode layers 10 and 11 to pump oxygen into the small gap a from the air compartment b being balanced by the ability of the electrode layers 4 and 5 to pump out oxygen from the small gap a into the exhaust pipe 1. If the position $V_3$ is selected connecting the electrode layers 4 and 5 to the constant current source $E_3$, the electromotive force e sensed at the output terminals 21 drops suddenly at an A/F ratio $\gamma'$ in the fuel-lean region as shown in FIG. 6 because the ability of the electrode layers 4 and 5 to pump out oxygen from the small gap a into the exhaust pipe 1 is greater than the ability of the electrode layers 10 and 11 to pump oxygen into the small gap a from the air compartment b.

The detector according to the first embodiment of the present invention makes use of the characteristics depicted in FIGS. 4 to 6. The abrupt change in the electromotive force e generated between the porous Pt electrode layers 8 and 9 of the electrochemical cell sensor element 12 may be used for controlling the A/F ratio of an internal combustion engine. By selecting the position $V_1$ of the switch 20, the characteristic shown in FIG. 4 wherein the EMF changes abruptly at a value near $\alpha'$ is obtained at the output terminals 21, and this abrupt change can be used for controlling the engine to operate at the value $\alpha'$. By properly selecting $V_2$ and $V_3$, the engine can be controlled to operate at values near the theoretical value of 14.7 and $\gamma'$, respectively. Stated more specifically, a reference point P is established between maximum and minimum EMFs so that output terminals 21 provide both a voltage that is higher than point P and a voltage that is lower than point P.

In the first embodiment described above, three constant current sources $E_1$, $E_2$ and $E_3$ which are connected to three different positions of the switch 20 are used to perform control over the A/F ratio of an internal combustion engine. It should be understood though that any number of constant current sources having any suitable output ratings may be used. If necessary, a constant current source which provides continuously or discretely variable current values may be employed for the purpose of fine control or measurement over the entire range of A/F ratio values of interest.

Figure 7:
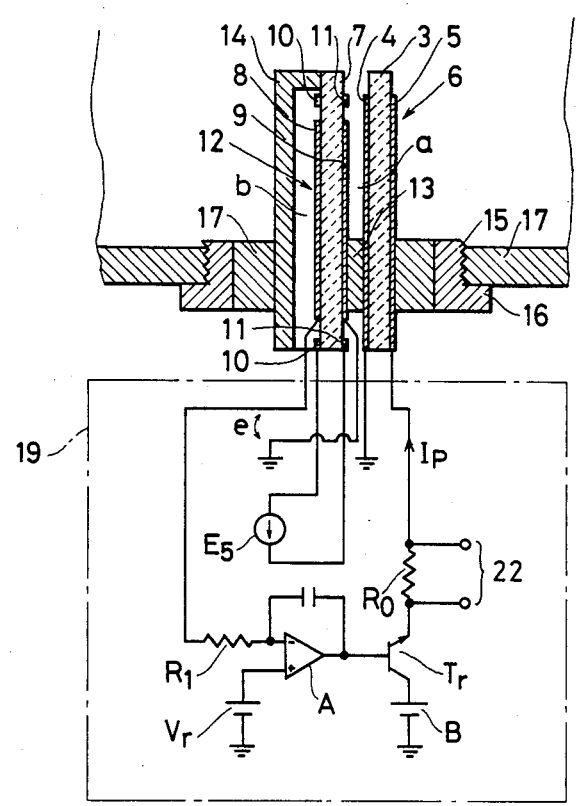
FIG. 7 shows, in cross section, an A/F ratio detector according to a second preferred embodiment of the present invention.

A modification of the electronic control unit 19 for use in association with the A/F ratio detector according to the first embodiment is illustrated in FIG. 7. The EMF e generated between the porous Pt electrode layers 8 and 9 of the electrochemical cell sensor element 12 is applied to the inverting input terminal of the operational amplifier A through a resistor $R_1$, and the amplifier produces an output proportional to the difference between e and a reference voltage $V_r$ applied to the noninverting input terminal of the amplifier. The output of the amplifier drives a transistor Tr to control the pump current $I_p$ flowing between the Pt electrode layers 4 and 5 of the pump element 6 in such a manner that $I_p$ is sufficient to maintain e at the constant level $V_r$. The control unit 19 also includes a resistor $R_0$ to provide output terminals 22 with an output signal corresponding to the pump current $I_p$ supplied from a d.c. source B. A constant current $E_5$ is connected between the porous Pt electrode layers 10 and 11 on the cell sensor element 12 in order to pump a given amount of oxygen into the small gap a from the air compartment b. The output of the amplifier A and its inverting input are connected by a capacitor C.

Figure 8:
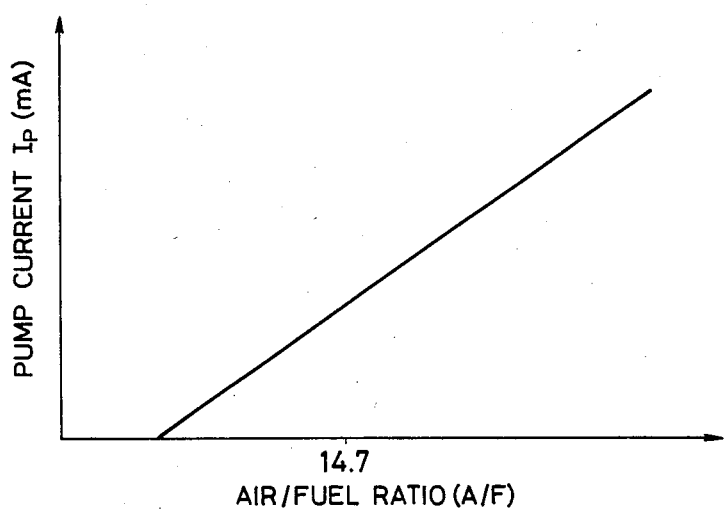
FIG. 8 is a characteristic curve for the second embodiment of the present invention showing the A/F ratio vs. the pump-out current $I_p$ flowing through the pump element, with both the pump-in current flowing through one pair of porous Pt electrode layers on the electrochemical cell sensor element and the electromotive force e of the other pair of porous Pt electrode layers on the sensor element being held constant.

A characteristic curve for the detector shown in FIG. 7 is illustrated in FIG. 8, which shows the profile of the pump current $I_p$ vs. A/F ratio, with both the reference voltage $V_r$ and EMF (e>0) held constant. The pump current $I_p$ flowing between the electrode layers 4 and 5 on the pump element 6 increases linearly as the A/F ratio increases from less-than-theoretical values (in the fuel-rich region) to greater-than-theoretical values (in the fuel-lean region).

The detector shown in FIG. 7 uses the characteristic depicted in FIG. 8. More specifically, an output signal indicating an A/F ratio corresponding to the pump current $I_p$ flowing through the pump element 6 is sensed at the output terminals 22 for the purposes of measuring accurately the A/F ratio of the internal combustion engine both in the fuel-rich region and in the fuel-lean region and of controlling the A/F ratio at any value in these regions.

The configuration of the detector probe 2 that can be used in the present invention is not limited to the one shown above in connection with the first and second embodiments, and various other configurations may be employed. The direction in which oxygen is caused to flow by means of the porous electrode layers 4 and 5 of the pump element, or one pair of electrode layers 8, 9 or 10, 11 on the electrochemical cell sensor element 12, may also be selected in various manners. Further, an air compartment such as one provided on the sensor element may be provided on the pump element. The current switching arrangement, A/F ratio sensing arrangement, and other components of the electronic control unit 19 are also not limited to those shown above and various other configurations may be employed.

In the first and second embodiments of FIGS. 1 and 7, the electrode layers 8, 10 or 9, 11 are separately or discretely deposited on the respective side faces of the sensor element 12 (between the layers 8 and 10 or between the layers 9 and 11). However, it is possible to utilize a suitable single electrode layer in common for the layers 8 and 10 or the layers 9 and 11 in place of the two separate layers.

Figure 9:
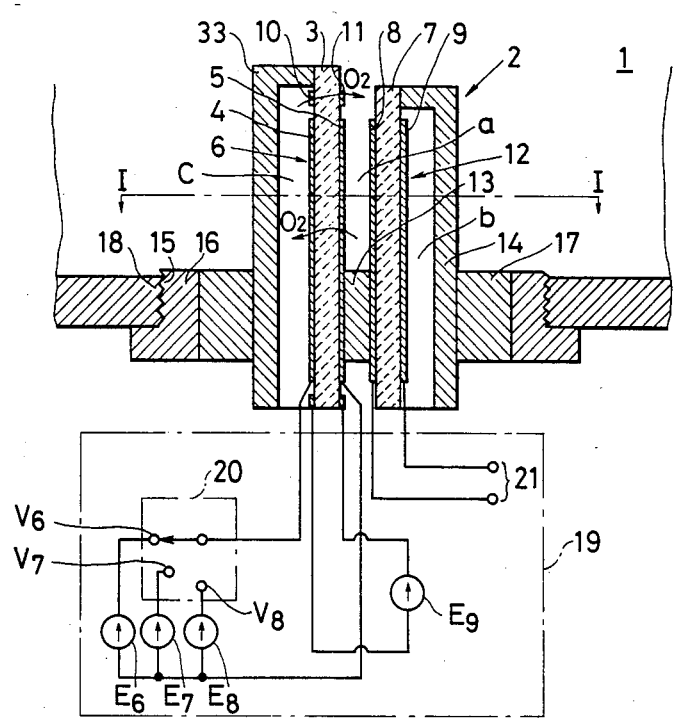
FIG. 9 shows, in cross section, an A/F ratio detector according to a third preferred embodiment of the present invention.
Figure 10:
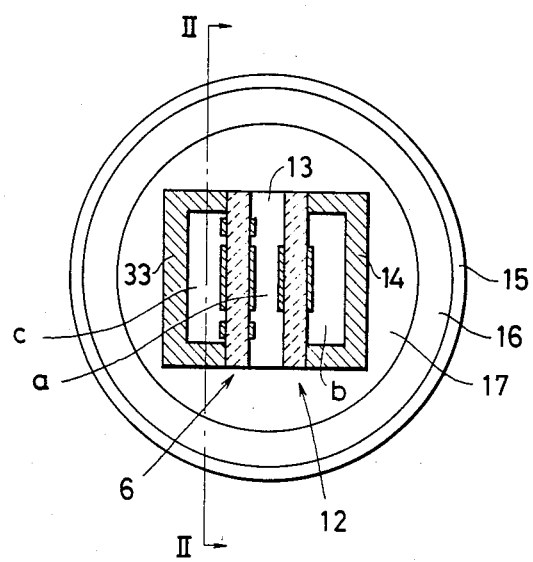
FIG. 10 is a cross section taken along a line I—I of FIG. 9.
Figure 11:
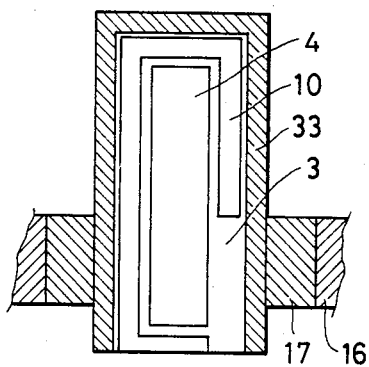
FIG. 11 is a cross section taken along a line II—II of FIG. 10.

FIGS. 9, 10 and 11 show an A/F ratio detector according to a third preferred embodiment of the invention. The detector is mounted in an exhaust pipe 1 of an internal engine. The probe 2 of the detector includes a solid-electrolyte oxygen pump element 6 and a solid-electrolyte oxygen-concentration-difference-actuated electrochemical cell sensor element 12. The pump element 6 consists of an ion-conductive solid-electrolyte plate 3 (about 0.5 mm thick and preferably made of stabilized zirconia) having two porous platinum electrode layers 4 and 10 formed on one side and two porous Pt electrode layers 5 and 11 formed on the other side. Each Pt layer has a thickness of about 20 $\mu$m and may be formed by a thick-film deposition technique. The electrochemical cell sensor element 12 also consists of an ion-conductive solid-electrolyte plate 7 (about 0.5 mm thick and preferably made of stabilized zirconia) having a porous platinum electrode layer 8 formed on one side and another porous Pt electrode layer 9 on the other side. The layers 4 and 5 on the electrolyte plate 3 together constitute a first pair of electrodes, and the layers 10 and 11 constitute a second pair. The first pair of electrodes 4 and 5 is formed at the center of the solid electrolyte plate 3, whereas the other pair of electrodes 10 and 11 is disposed around and spaced from the electrodes 4 and 5.

The pump element 6 and the sensor element 12 are mounted side by side in the exhaust pipe 1 with a gap a therebetween, typically about 0.1 mm in width, and are fixed together by filling the gap at the base portion with a heat-resistive and insulating spacer 13. An adhesive filler may be used as the spacer. The peripheral edge of the solid electrolyte plate 3 on the side opposite the gap from the sensor element 12 is provided with a wall 33 made of a heat-resistive and gas-impermeable material such as a metal or ceramic to form an air compartment c which is open to the atmosphere. This wall 33 is sealed around the porous Pt electrode layers 4 and 10, except for their base portions, so that these layers can communicate with the atmosphere. The peripheral edge of the solid electrolyte plate 7 on the side opposite the gap from the pump element 6 is provided with a wall 14 which is also made of a heat-resistive and gas-impermeable material such as a metal or ceramic to form an air compartment b which is open to the atmosphere. The wall 14 is sealed around the porous Pt electrode layer 9, except for its base portion, so that this layer can communicate with the atmosphere.

A support 16 with a male thread 15 is fixed around the base portion of the combined pump element 6, sensor element 12, as well as walls 33 and 14 by a heat-resistive and insulating adhesive member 17. The probe 2 is securely mounted in the exhaust pipe 1 by engaging the male thread 15 with a female thread 18 in the exhaust pipe 1.

An example of an electronic control unit for use in association with the detector according to the third embodiment of the present invention is indicated in FIG. 9 by reference numeral 19. The porous Pt electrode layers 4 and 5 of the pump element 6 are connected to a switch 20 which can selectively actuate constant current sources $E_6$, $E_7$ and $E_8$ ($E_6 < E_7 < E_8$) that provide currents for pumping oxygen out of the small gap a into the air compartment c. The switch 20 has three positions $V_6$, $V_7$ and $V_8$ which respectively provide connection to the three constant current sources $E_6$, $E_7$ and $E_8$. The other pair of electrodes 10 and 11 of the pump element 6 are connected to a constant current source $E_9$ for pumping oxygen into the small gap a from the air compartment c. In the embodiment shown, the ability of the current source $E_7$ to pump oxygen out of the small gap a into the air compartment c is made substantially equal to the ability of the current source $E_9$ to pump oxygen into the small gap a from the air compartment c.

The porous Pt electrode layers 8 and 9 on the electrochemical cell sensor element 12 are connected at one end to output terminals 21 for sensing the electromotive force e generated across the electrode layers.

The operation of the detector shown in FIG. 9 is as follows. It is first assumed that position $V_6$ of the switch 20 is selected, connecting the constant current source $E_6$ to the pair of porous Pt electrode layers 4 and 5 of the pump element 6 in the detector probe 2 mounted in the exhaust pipe 1. Since the ability of the electrode layers 4 and 5 to pump out oxygen from the small gap a into the air compartment c is less than the ability of the other pair of porous Pt electrode layers 10 and 11 on the pump element 6 to pump oxygen into the small gap a from the air compartment c, the electromotive force 3 generated across the porous Pt electrode layers 8 and 9 of the electrochemical cell sensor element 12 due to the difference in partial oxygen pressure between the air compartment b and small gap a and which is sensed at the output terminals 21 drops suddenly at a certain A/F ratio in the fuel-rich region to provide a characteristic identical to that depicted in FIG. 4. When the switch 20 is set to the position $V_7$ connecting the Pt electrode layers 4 and 5 to the current source $E_7$, the electromotive force e sensed at the output terminals 21 also drops suddenly, but this time near the theoretical 14.7 (as in FIG. 5), which is a critical point for the concentration of oxygen in the exhaust pipe. This is due to the ability of the electrode layers 10 and 11 to pump oxygen into the small gap a from the air compartment c balancing with the ability of the electrode layers 4 and 5 to pump out oxygen from the small gap a into the air compartment c. If the position $V_8$ is selected connecting the electrode layers 4 and 5 to the constant current source $E_8$, the electromotive force e sensed at the output terminals 21 drops suddenly at a certain A/F ratio in the fuel-lean region. In this case, a characteristic similar to that depicted in FIG. 6 is obtained because the ability of the electrode layers 4 and 5 to pump out oxygen from the small gap a into the air compartment c is greater than the ability of the electrode layers 10 and 11 to pump oxygen into the small gap a from the air compartment c.

As can readily be understood from the discussion above, the detector according to the third embodiment of the present invention also makes use of the characteristics depicted in FIGS. 4 to 6. The abrupt change in the electromotive force e generated between the porous Pt electrode layers 8 and 9 of the electrochemical cell sensor element 12 may be used in controlling the A/F ratio of an internal combustion engine. By selecting the position $V_6$ of the switch 20, the characteristic shown in FIG. 4 wherein the EMF changes abruptly at a value near a certain value in the fuel-rich region is obtained at the output terminals 21, and this abrupt change can be used for controlling the engine at that value. By selecting $V_7$ and $V_8$, the engine can be controlled to operate at values near the theoretical value of 14.7 and a certain value in the fuel-lean region, respectively.

In the third embodiment shown above, three constant current sources $E_6$, $E_7$ and $E_8$ which are selectively connected to three different positions of switch 20 are used to perform control over the A/F ratio of an internal combustion engine. It should be understood though that any number of constant current sources having any suitable output ratings may be used. If necessary, a constant current source which provides continuously or discretely variable current values may be employed for the purpose of fine control or measurement over the entire range of A/F ratio values of interest.

Figure 12:
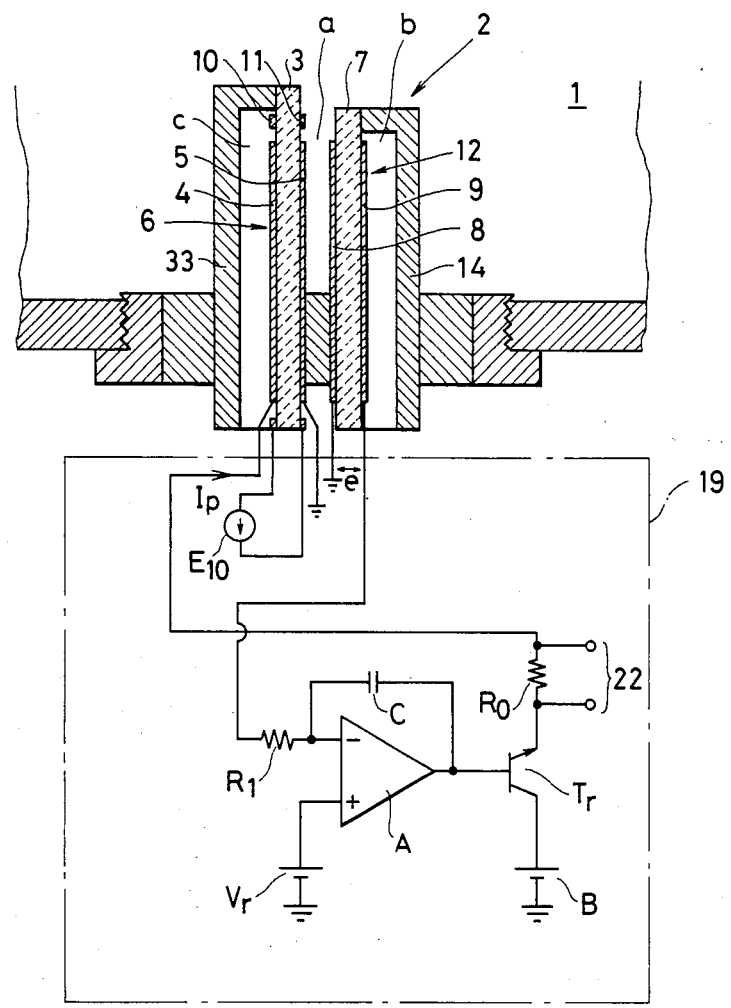
FIG. 12 shows, in cross section, an A/F ratio detector according to a fourth preferred embodiment of the present invention.

A modification of the electronic control unit for use in association with the A/F ratio detector according to the third embodiment is illustrated in FIG. 12. The EMF e generated between the porous Pt electrode layers 8 and 9 of the electrochemical cell sensor element 12 is applied to the inverting input terminal of the operational amplifier A through a resistor $R_1$, and the amplifier produces an output proportional to the difference between e and a reference voltage $V_r$ applied to the noninverting input terminal of the amplifier. The output of the amplifier drives a transistor Tr to control the pump current $I_p$ flowing between the Pt electrode layers 4 and 5 of the pump element 6 in such a manner that $I_p$ is sufficient to maintain e at the constant level $V_r$. The control unit 19 also includes a resistor $R_0$ to provide the output terminals 22 with an output signal corresponding to the pump current $I_p$ supplied from a d.c. source b. A constant current source $E_{10}$ is connected between the porous Pt electrode layers 10 and 11 of the pump element 6 in order to pump a given amount of oxygen into the small gap a from air compartment c. The output of the amplifier A and its inverting input are connected by a capacitor C.

The A/F ratio detector shown in FIG. 12 produces characteristics substantially the same as those illustrated in FIG. 8. When the reference voltage $V_r$ in FIG. 12 is held constant and the electromotive force e across the electrode layers 8 and 9 on the sensor element 12 is also held constant (e>0), the pump current $I_p$ flowing between the electrode layers 4 and 5 of the pump element 6 increases linearly as the A/F ratio increases from less-than-theoretical values (in the fuel-rich region) to greater-than-theoretical values (in the fuel-lean region).

The detector according to the fourth embodiment makes use of the characteristics of the same type as shown in FIG. 8. More specifically, an output signal indicating an A/F ratio corresponding to the pump current $I_p$ flowing through the pump element 6 is sensed at the output terminals 22 for the purposes of measuring accurately the A/F ratio of an internal combustion engine both in the fuel-rich region and in the fuel-lean region and of controlling the A/F ratio at any value in these regions.

The configuration of the detector probe 2 that can be used in the present invention is not limited to the one shown above in connection with the third and fourth embodiments, and various other configurations may be employed. Further, the air compartment formed on the pump element is not always necessary because oxygen can be supplied to a certain degree from the exhaust gas by the pumping action of the pump element. The direction in which oxygen is caused to flow by the pumping action of the first pair of porous electrode layers 4 and 5 of the pump element 6, or the second pair of electrode layers 10 and 11 may also be selected in various manners. The current switching arrangement, A/F ratio sensing arrangement and other components of the electronic control unit 19 are also not limited to those shown above, and various other designs may be employed.

In the third and fourth embodiments of FIGS. 9 and 12, the electrode layers 4 and 10 or 5 and 11 are separately or discretely deposited on the respective side faces of the pump element 6 (between the layers 4 and 10 or between the layers 5 and 11). However, it is possible to utilize a suitable single electrode layer in common for the layers 4 and 10 or the layers 5 and 11 in place of the two separate layers.

In the detection probe of the above embodiments of the present invention, the pump element and the sensor element are mounted side by side in the exhaust pipe with a gap therebetween and are fixed together by filling the gap at the base portions with a spacer.

However, the present invention is not limited to the configuration of open edges of the pump element and the sensor element except at base portions thereof. For example, it is possible to provide support members between the solid-electrolyte plates of the pump element and the sensor element for more readily regulating the gap dimensions as far as the small gap sufficiently communicates with ambient gases through small apertures formed by the support members and the solid-electrolyte plates not to result in a considerable reduction of responsivity.

Furthermore, in the embodiments of FIGS. 1 and 7, at least one small aperture may be perforated into the central region of the solid-electrolyte plate of the pump element in order to improve communications between the small gap and ambient gases.

The characteristic described above provided by the detector of the present invention may be used either individually or in combination for the purpose of measurement of and feedback control over the operating A/F ratio throughout the dynamic range.

What is claimed is:

1. An A/F ratio detector comprising: a solid electrolyte oxygen pump element having porous electrodes formed on both sides of an oxygen-ion-conductive solid electrolyte and a solid-electrolyte oxygen-concentration-difference-actuated electrochemical cell sensor element disposed to face said pump element with a small gap therebetween and which has two pairs of porous electrodes formed on an oxygen-ion-conductive solid electrolyte with the electrodes of each pair being disposed on opposite sides of said electrolyte, said small gap communicating with ambient gases, means defining an air compartment open to the atmosphere on that side of at least said electrochemical cell sensor element of said two elements opposite said small gap, means for applying a first current between one of said electrodes of one of said two pairs and said electrodes of said pump element, said first current being of such direction that oxygen is supplied into said small gap, and means for applying a second current between one of said electrodes of said one of said two pairs and said electrodes of said pump element other than said electrodes to which said first current is applied, said second current being of such direction that oxygen is pumped out from said small gap, one of an electromotive force generated by the other pair of electrodes of said electrochemical cell sensor element, said second current and said first current providing an output signal for A/F ratio detection.

2. The A/F ratio detector of claim 1, wherein said two pairs of porous electrodes formed on said oxygen-ion-conductive solid electrolyte comprise first and second pairs of electrodes with said first pair being disposed at a substantially central part of said electrolyte and said second pair at least partially surrounding said first pair, said first current being applied to said second pair of electrodes.

3. The A/F ratio detector of claim 1, further comprising constant first current source means for applying a current of such direction that oxygen is supplied into said small gap between the electrodes of one of said pairs, and variable second current source means for applying a current of a selectable magnitude of such direction that oxygen is pumped out from said small gap between said electrodes of said pump element, a voltage produced between said electrodes of the other pair providing said output signal for A/F ratio detection.

4. The A/F ratio detector of claim 1, further comprising current source means for passing a constant current between said electrodes of one of said pairs, said constant current being of such direction that oxygen is supplied into said small gap, and negative feedback control circuit means for maintaining an electromotive force generated between the other pair of said electrodes of said electrochemical cell sensor element at a constant value by adjusting the magnitude of an adjustable current applied between said electrodes of said pump element, said adjustable current being of such direction that oxygen is pumped out from said small gap, said adjustable current providing said output signal for A/F ratio detection.

5. An A/F ratio detector comprising: a solid-electrolyte oxygen pump element having two pairs of porous electrodes formed on an oxygen-ion-conductive solid electrolyte with the electrodes of each paid being disposed on opposite sides of said electrolyte, and a solid electrolyte oxygen-concentration-difference-actuated electrochemical cell sensor element disposed to face said pump element with a small gap therebetween and which has porous electrodes formed on both sides of an oxygen-ion-conductive solid electrolyte, said small gap communicating with ambient gases, means defining an air compartment open to the atmosphere on that side of at least the electrochemical cell sensor element opposite said small gap, means for applying a first current between said electrodes of one of said two pairs, said first current being of such direction that oxygen is supplied into said gap, and means for applying a second current between said electrodes of the other pairs, said second current being of such direction that oxygen is pumped out from said small gap, one of an electromotive force generated by said electrodes of said electrochemical cell sensor element, said second current and said first current providing an output signal for A/F ratio detection.

6. The A/F ratio detector of claim 5, wherein said two pairs of porous electrodes formed on said oxygen-ion-conductive solid electrolyte comprise first and second pairs of electrodes with said first pair being disposed at a substantially central part of said electrolyte and said second pair at least partially surrounding said first pair, said first current being applied to said second pair of electrodes.

7. The A/F ratio detector of claim 5, further comprising constant first current source means for applying a current between the electrodes of one of said pairs, said constant current being of such direction that oxygen is supplied into said small gap, and variable second current source means for applying a current of a selectable magnitude between the electrodes of the other pair, said selectable current being of such direction that oxygen is pumped out from said small gap, a voltage produced between said electrodes of said electrochemical cell sensor element providing said output signal for A/F ratio detection.

8. The A/F ratio detector of claim 5, further comprising current source means for passing a constant current between the electrodes of one of said pairs, said constant current being of such direction that oxygen is supplied into said small gap, and negative feedback control circuit means for maintaining an electromotive force generated between the electrodes of said electrochemical cell sensor element at a constant value by adjusting the magnitude of a an adjustable current applied between the electrodes of the other pair on said pump element, said adjustable current being of such direction that oxygen is pumped out from said small gap, said adjustable current providing said output signal for A/F ratio detection.

* * * * *